(12) United States Patent
Karinka et al.

(10) Patent No.: US 6,863,800 B2
(45) Date of Patent: Mar. 8, 2005

(54) ELECTROCHEMICAL BIOSENSOR STRIP FOR ANALYSIS OF LIQUID SAMPLES

(75) Inventors: Shridhara Alva Karinka, Lowell, MA (US); Geoffrey Roger Chambers, Middlesex (GB); Gurdial Sanghera, Oxon (GB)

(73) Assignee: Abbott Laboratories, Abbott Park, IL (US)

( * ) Notice: Subject to any disclaimer, the term of this patent is extended or adjusted under 35 U.S.C. 154(b) by 265 days.

(21) Appl. No.: 10/062,313

(22) Filed: Feb. 1, 2002

(65) Prior Publication Data

US 2003/0146110 A1 Aug. 7, 2003

(51) Int. Cl.$^7$ ............................................. G01N 27/327
(52) U.S. Cl. ............... 205/777.5; 205/792; 204/403.14; 204/403.11
(58) Field of Search ....................... 204/403.01, 403.04, 204/403.09, 403.1, 403.11, 403.13, 403.14, 411, 403.05, 403.06; 205/777.5, 778

(56) References Cited

U.S. PATENT DOCUMENTS

| 4,897,173 A | 1/1990 | Nankai et al. ......... 204/403.05 |
| 5,108,564 A | 4/1992 | Szuminsky et al. ...... 205/777.5 |
| 5,120,420 A | 6/1992 | Nankai et al. ......... 204/403.11 |
| 5,171,689 A | 12/1992 | Kawaguri et al. ....... 204/403.1 |
| 5,185,256 A | 2/1993 | Nankai et al. .............. 435/174 |

(List continued on next page.)

FOREIGN PATENT DOCUMENTS

| WO | 97/08544 | 3/1997 | .......... G01N/27/42 |
| WO | 99/19507 | 4/1999 | ............ C12Q/1/00 |

OTHER PUBLICATIONS

James R. Sandifer, "Electroanalytical Techniques," Kirk—Othmer Encyclopedia of Chemical Technology, 4$^{th}$ ed., vol. 9, John Wiley & Sons, Inc. (New York: 1994) pp. 88–111.

Peter T. Kissinger, "Introduction to Analog Instrumentation," Laboratory Techniques in Electroanalytical Chemistry, Marcel Dekker, Inc. (New York: 1984) pp. 163–234, month currently unknown.

*Primary Examiner*—Alex Noguerola
(74) *Attorney, Agent, or Firm*—David L. Weinstein (57) ABSTRACT

A biosensor in the form of a strip. In one embodiment, the biosensor strip comprises an electrode support, a first electrode, i.e., a working electrode, a second electrode, i.e., a counter electrode, and a third electrode, i.e., a reference electrode. Each of the electrodes is disposed on and supported by the electrode support. Each of the electrodes is spaced apart from the other two electrodes. The biosensor strip can include a covering layer, which defines an enclosed space over the electrodes. This enclosed space includes a zone where an analyte in the sample reacts with reagent(s) deposited at the working electrode. This zone is referred to as the reaction zone. The covering layer has an aperture for receiving a sample for introduction into the reaction zone. The biosensor strip can also include at least one layer of mesh interposed in the enclosed space between the covering layer and the electrodes in the reaction zone. This layer of mesh facilitates transporting of the sample to the electrodes in the reaction zone. In another embodiment, a biosensor strip can be constructed to provide a configuration that will allow the sample to be introduced to the reaction zone by action of capillary force. In this embodiment, the layer of mesh can be omitted. The invention also provides a method for determining the concentration of glucose in a sample of whole blood by using the biosensor of this invention.

12 Claims, 5 Drawing Sheets

U.S. PATENT DOCUMENTS

| | | | |
|---|---|---|---|
| 5,288,636 A | | 2/1994 | Pollmann et al. ...... 204/403.04 |
| 5,494,562 A | * | 2/1996 | Maley et al. ................ 257/414 |
| 5,508,171 A | | 4/1996 | Walling et al. ........... 205/777.5 |
| 5,512,159 A | | 4/1996 | Yoshioka et al. ...... 204/408.08 |
| 5,571,395 A | * | 11/1996 | Park et al. ............... 204/403.1 |
| 5,650,062 A | | 7/1997 | Ikeda et al. .................. 205/778 |
| 5,653,863 A | | 8/1997 | Genshaw et al. ........ 205/777.5 |
| 5,672,256 A | * | 9/1997 | Yee .......................... 422/82.01 |
| 5,759,364 A | | 6/1998 | Charlton et al. .......... 204/403.1 |
| 5,997,817 A | | 12/1999 | Crismore et al. ........ 204/403.1 |
| 6,153,069 A | | 11/2000 | Pottgen et al. ......... 204/403.11 |
| 6,245,215 B1 | | 6/2001 | Douglas et al. .............. 205/775 |
| 6,287,451 B1 | * | 9/2001 | Winarta et al. ........... 205/777.5 |
| 6,309,526 B1 | * | 10/2001 | Fujiwara et al. ....... 204/403.14 |
| 6,592,745 B1 | * | 7/2003 | Feldman et al. .......... 205/777.5 |

* cited by examiner

ELECTROCHEMICAL BIOSENSOR STRIP FOR ANALYSIS OF LIQUID SAMPLES

BACKGROUND OF THE INVENTION

1. Field of the Invention

The invention relates to biosensors for performing electrochemical analysis to determine concentrations of analytes in liquids.

2. Discussion of the Art

Electrochemical assays for determining the concentrations of enzymes or their substrates in complex mixtures of liquids have been developed. Biosensor strips (i.e., biosensors in the form of strips) are useful in medical research and in external testing. In medical research, biosensor strips can function in an invasive manner (i.e., as probes that come into contact with a body fluid, such as whole blood or subcutaneous fluid). In external testing, biosensor strips can function in a non-invasive manner (i.e., as strips that come into contact with blood withdrawn by a syringe or a lancing device). In particular, biosensor strips for biomedical applications (e.g., whole blood analyses) have been developed for the determination of glucose levels in biological samples. In general, biosensor strips comprise electrochemical cells in which there can be working electrodes, counter electrodes, and reference electrodes. The potential of the working electrode is maintained at a constant value relative to that of the reference electrode.

Conventional electrochemical systems having three electrodes employ (1) a working electrode, (2) a reference electrode, and (3) a counter electrode. The reaction that takes place at the working electrode is the reaction that is required to be monitored and controlled. The functions of the reference and counter electrodes are to ensure that the working electrode actually experiences the desired conditions, i.e. the correct potential intended to be applied. The function of the reference electrode is to measure the potential at the interface of the working electrode and the sample as accurately as possible. In an ideal situation, no current passes through the reference electrode. The function of the counter electrode is to ensure that the correct potential difference between the reference electrode and the working electrode is being applied. The potential difference between the working electrode and the reference electrode is assumed to be the same as the desired potential at the working electrode. If the potential measured at the working electrode is not the potential desired at the working electrode, the potential that is applied between the counter electrode and working electrode is altered accordingly, i.e., the potential is either increased or decreased. The reaction at the counter electrode is also equal and opposite to the charge transfer reaction occurring at the working electrode, i.e., if an oxidation reaction is occurring at the working electrode then a reduction reaction will take place at the counter electrode, thereby allowing the sample to remain electrically neutral.

All commercially available electrochemical biosensor strips for determining the concentration of glucose employ two electrodes. In a two-electrode system, there are (1) a working electrode and (2) a dual-purpose reference/counter electrode. The second electrode is called a dual-purpose reference/counter electrode because this electrode acts as a reference electrode as well as a counter electrode. No current passes through an ideal reference electrode, and such an electrode maintains a steady potential; current does pass through a dual-purpose reference/counter electrode, and thus, the dual-purpose reference/counter electrode does not maintain a steady potential during the measurement. At low currents and/or at short durations of time for measurement, the shift in potential is small enough such that the response at the working electrode is not significantly affected, and hence the dual-purpose reference/counter electrode is designated a dual-purpose reference/counter electrode. The dual-purpose reference/counter electrode continues to carry out the function of a counter electrode; however, in this case, the potential that is applied between the dual-purpose reference/counter electrode and the working electrode cannot be altered to compensate for changes in potential at the working electrode. In other words, while conventional electrochemical measurements require three electrodes, in all commercially available biosensor strips, there are only two electrodes, wherein one of the electrodes performs two functions—the reference function and the counter function.

As indicated previously, a reference electrode provides a reference for the voltage applied at the working electrode. The voltage applied must be sufficient to oxidize or reduce the species (molecule or ion) of interest at the surface of the working electrode. The voltage required is determined by the ease of removing or adding an electron to the species of interest. Because this voltage is applied externally (by means of a potentiostat or battery), the reference point should be maintained at a constant value. If the value of the reference point changes with time, the external voltage applied should be varied accordingly. Commercially available biosensor strips are very sensitive to the quality of the electrode that performs two functions (the reference function and the counter function). If that electrode is of poor quality, the voltage applied at the working electrode (by means of a battery or potentiostat) will not be maintained at a constant value, resulting in variation in the response of the biosensor strip from sample to sample. This variation depends on the hematocrit (which affects solution resistance) and concentration of the analyte (which affects current). In most electrochemical measurements, the current is measured at a constant applied voltage.

In a biosensor strip, the electrodes are separated from each other. The space between the electrodes results in the loss of voltage control at the working electrode. The voltage experienced at the working electrode therefore is lower than that applied. The difference between the voltage applied and the voltage experienced at the working electrode is a product of the current passing between the dual-purpose reference/counter electrode and the working electrode and the resistance of the solution. Also, on account of the current passing through the circuit, the dual-purpose reference/counter electrode becomes polarized. In other words, the flow of current through the dual-purpose reference/counter electrode brings about a reduction reaction at the electrode, thereby changing the chemical composition of the dual-purpose reference/counter electrode. This change in chemical composition brings about a change in the potential at the dual-purpose reference/counter electrode, and hence a change in the voltage applied.

A biosensor strip having three electrodes would be preferred in any electrochemical measurement that involves the application of an external voltage and measurement of current. However, due to constraints of sample volume (lower volume requirements), all electrochemical biosensor strips commercially available use only two electrodes. Precise control of the voltage difference between the working electrode and the reference electrode must be maintained, but such control is difficult to achieve in a two-electrode system.

SUMMARY OF THE INVENTION

In one aspect, this invention provides a biosensor in the form of a strip. In one embodiment, the biosensor strip comprises an electrode support, a first electrode, i.e., a working electrode, a second electrode, i.e., a counter electrode, and a third electrode, i.e., a reference electrode. Each of the electrodes is disposed on and supported by the electrode support. Each of the electrodes is spaced apart from the other two electrodes. The biosensor strip can include a covering layer, which defines an enclosed space over the electrodes. This enclosed space includes a zone where an analyte in the sample reacts with reagent(s) deposited at the working electrode. This zone is referred to as the reaction zone. The covering layer has an aperture for receiving a sample for introduction into the reaction zone. The biosensor strip can also include at least one layer of mesh interposed in the enclosed space between the covering layer and the electrodes in the reaction zone. This layer of mesh facilitates transporting of the sample to the electrodes in the reaction zone.

The electrodes can be arranged in any order, with respect to the order in which the sample contacts each electrode. However, it is preferred to position the counter electrode downstream of the working electrode and the reference electrode so that the reference electrode and the working electrode come into contact with the sample before the counter electrode does. It is preferred that the working electrode be completely covered by the sample before the analyte monitor indicates that the sample has been applied.

In another embodiment, biosensor strip can be constructed to provide a configuration that will allow the sample to be introduced to the reaction zone by action of capillary force. In this embodiment, the layer of mesh can be omitted. The biosensor strip comprises an electrode support, a cover layer, a first electrode, i.e., a working electrode, a second electrode, i.e., a counter electrode, and a third electrode, i.e., a reference electrode. At least one of the electrodes is disposed on and supported by the electrode support, and at least one of the remaining two electrodes is disposed on and supported by the cover layer. The electrode support and the cover layer are joined by adhesion, such as, for example, by a layer of pressure sensitive adhesive. The layer of pressure sensitive adhesive also serves to provide a space, i.e., a capillary, between the electrode support and the cover layer. The sample is introduced into the reaction zone by means of flow through this space. As in the previously described embodiment, each of the electrodes is spaced apart from the other two electrodes. In this embodiment, it is preferred that the layer of mesh be omitted.

In another aspect, the invention provides a method for determining the concentration of glucose in a sample of whole blood by using the biosensor of this invention. In a mode of measurement employing three electrodes, no current flows between the working electrode and the reference electrode, and consequently, there is no difference between the voltage applied and the voltage experienced at the working electrode. The counter electrode becomes polarized but does not affect the measurement of current. The change in the composition of the chemistry at the surface of the counter electrode does not interfere with the biochemical or electrochemical reaction at the working electrode.

Other features and advantages of the invention will be apparent from the descriptions of the embodiments thereof.

DETAILED DESCRIPTION

As used herein, the expression "working electrode" means an electrode where the reaction of interest takes place. The current is proportional to the concentration of an analyte, e.g., glucose, at the working electrode. The expression "working ink" means the formulation containing the reagents for carrying out the reaction of interest. Typically, the working ink is deposited on a layer of electrically conductive material to form the working electrode. In the case of glucose, the working ink contains both a redox mediator and a substance for reacting with the analyte, e.g., glucose oxidase. Depending upon the nature of the analyte, the substance for reacting with the analyte can be an enzyme or a substrate for an enzyme. The expressions "redox mediator", "mediator", and the like, mean any substance that can oxidize or reduce another molecule, typically an enzyme. Redox mediators relay the information of an oxidation/reduction reaction from an enzyme to an electrode. The expression "reaction zone" means that portion of the biosensor strip wherein the liquid sample contacts the working, reference, and counter electrodes. The reaction zone further includes the reactive chemical(s), i.e., the reagent(s) that react with an analyte in the liquid sample.

Figure 1:
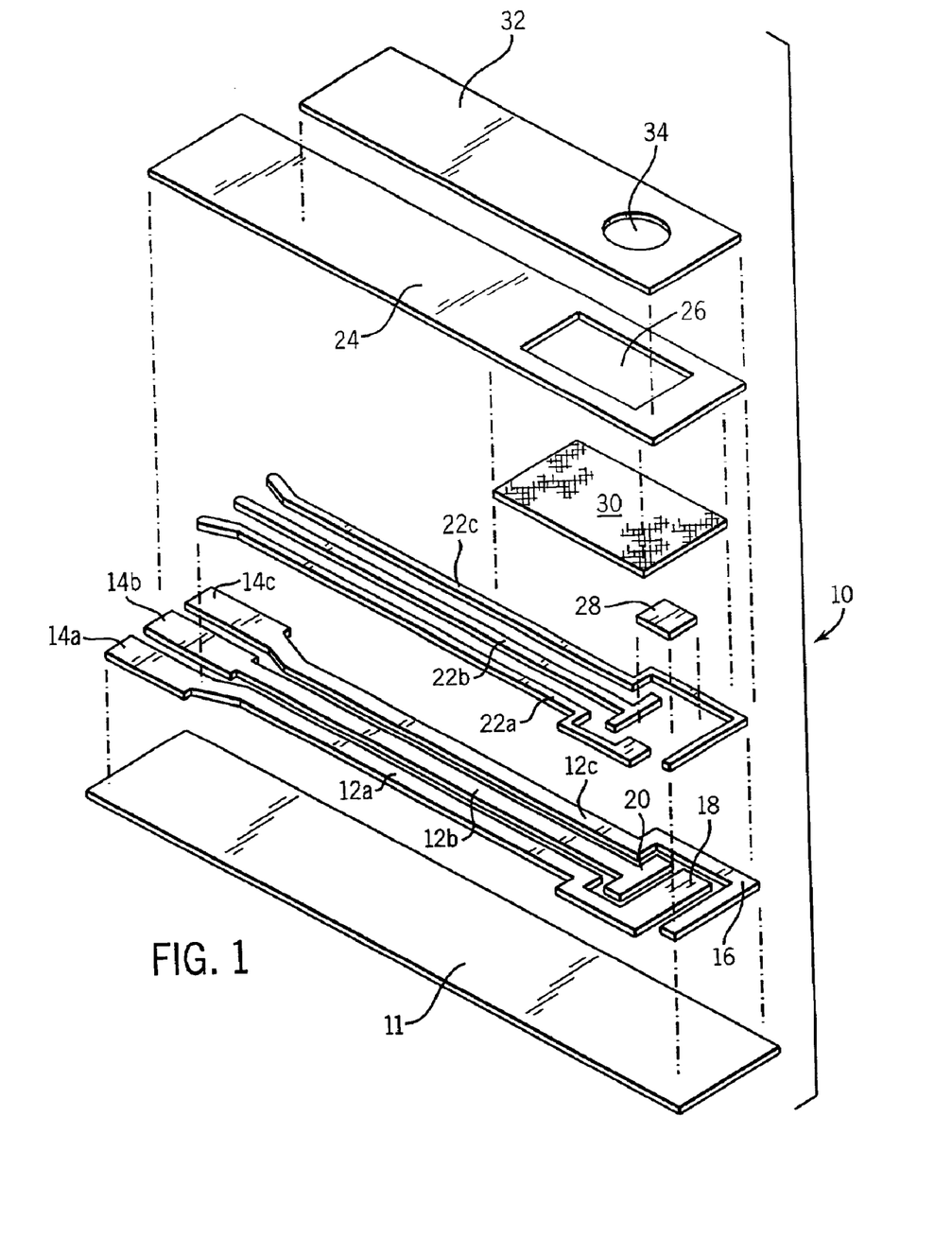
FIG. 1 is an exploded view of a biosensor strip according to one embodiment of this invention.

A biosensor strip 10 suitable for this invention is illustrated in FIG. 1. Referring to FIG. 1, an electrode support 11, preferably an elongated strip of polymeric material (e.g., polyvinyl chloride, polycarbonate, polyester, or the like) supports three tracks 12a, 12b, and 12c of electrically conductive ink, preferably comprising carbon. These tracks 12a, 12b, and 12c determine the positions of electrical contacts 14a, 14b, and 14c, a reference electrode 16, a working electrode 18, and a counter electrode 20. The electrical contacts 14a, 14b, and 14c are insertable into an appropriate measurement device (not shown).

Each of the elongated portions of the conductive tracks 12a, 12b, and 12c can optionally be overlaid with a track 22a, 22b, and 22c of conductive material, preferably made of a mixture comprising silver particles and silver chloride particles. The enlarged exposed area of track 22b overlies the reference electrode 16. A layer of a hydrophobic electrically insulating material 24 further overlies the tracks 22a, 22b, and 22c. The positions of the reference electrode 16, the working electrode 18, the counter electrode 20, and the electrical contacts 14a, 14b, and 14c are not covered by the layer of hydrophobic electrically insulating material 24. This hydrophobic electrically insulating material 24 serves to prevent short circuits. The layer of hydrophobic electrically insulating material 24 has an opening 26 formed therein. This opening 26 provides the boundary for the reaction zone of the biosensor strip 10. Because this insulating material is hydrophobic, it can cause the sample to be restricted to the portions of the electrodes in the reaction zone. The working electrode 18 comprises a layer of a non-reactive electrically conductive material on which is deposited a layer 28 containing a working ink for carrying out an oxidation-reduction reaction. At least one layer of mesh 30 overlies the electrodes. This mesh layer 30 protects the printed components from physical damage. The mesh layer 30 also helps the sample to wet the electrodes by reducing the surface tension of the sample, thereby allowing it to spread evenly over the electrodes. A cover 32 encloses the surfaces of the electrodes that are not in contact with the electrode support 11. This cover 32 is a liquid impermeable membrane. The cover 32 includes a small aperture 34 to allow access of the applied sample to the underlying mesh layer 30.

The layer of working ink 28 is deposited on that portion of the electrically conductive material of the working electrode 18 where the oxidation-reduction reaction is to take place when a sample is introduced to the biosensor strip 10. The layer of the working ink 28 can be applied to the working electrode 18 as a discrete area having a fixed length. The working ink comprises reagent(s) that is responsive to the analyte of interest deposited on the non-reactive electrically conductive material. Typical analytes of interest include, for example, glucose and ketone bodies. Typical non-reactive electrically conductive materials include, for example, carbon, platinum, palladium, and gold. A semi-conducting material such as indium doped tin oxide can be used as the non-reactive electrically conductive material. In preferred embodiments, the working ink comprises a mixture of a redox mediator and an enzyme. Alternatively, instead of an enzyme, the working ink can contain a substrate that is catalytically reactive with an enzyme to be assayed. For example, when the analyte to be measured is glucose in blood, the enzyme is preferably glucose oxidase, and the redox mediator is preferably ferrocene or a derivative thereof. Other mediators that are suitable for use in this invention include a ferricyanide salt and a phenanthroline quinone or a derivative thereof. In the biosensor strips of this invention, the reagent(s) are preferably applied in the form of ink containing particulate material and having binder(s), and, accordingly, does not dissolve rapidly when subjected to the sample. In view of this feature, the oxidation-reduction reaction will occur at the interface of working electrode 18 and the sample. The glucose molecules diffuse to the surface of the working electrode 18 and react with the enzyme/mediator mixture.

In addition to being applied to the working electrode 18, a layer of the working ink can be applied to any of the other electrodes, when desired, as a discrete area having a fixed length.

The thickness of the layer of non-reactive electrically conductive material is determined by the method of applying the layer. In the case of a layer deposited by printing, e.g., screen-printing, the thickness of the layer typically ranges from about 10 micrometers to about 25 micrometers. In the case of a layer deposited by vapor deposition, the thickness of the layer typically ranges from about less than 1 micrometer to about 2 micrometers. The layer of the working ink 28 that has been deposited on the working electrode 18 typically has a dry thickness of from about 2 to about 50 micrometers, preferably from about 10 to about 25 micrometers. The actual dry thickness of the deposited layer of the working ink 28 will depend to some extent upon the technique used to apply the working ink. For example, a thickness of from about 10 to about 25 micrometers is typical for a layer of working ink applied by means of screen-printing.

The reference electrode 16 is typically formed by screen-printing a mixture comprising a mixture of silver and silver chloride on the electrode substrate 11. For materials to which such a mixture does not readily adhere, it is preferred to deposit a layer of carbon on the electrode support to act as a primer layer for the mixture. This mixture is often referred to as ink. The mixture typically has a carrier comprising an organic solvent. Alternatives to the mixture of silver and silver chloride include mixtures of Ag and AgBr, mixtures of Ag and AgI, and mixtures of Ag and $Ag_2O$. The printed layer associated with the reference electrode 16 extends to partially cover the track of the carbon layer associated with the reference electrode 16, where the printed layer extends into the reaction zone. It is preferred to cover parts of the tracks 12a, 12b, and 12c outside the reaction zone with the mixture of silver and the silver compound associated therewith, so that the total electrical resistance of each track is reduced. Because no current flows through the reference electrode 16, non-classical reference electrodes can be used as the reference electrode. These non-classical electrodes can be formed either by simply employing a conductive material, such as, for example, carbon, platinum, or palladium, as the reference electrode or by having the working ink deposited on the conductive material that forms the reference electrode. The reference electrode 16 preferably has equal or smaller dimensions compared to those of the working electrode 18.

If the working ink is deposited on a conductive material to form the reference electrode 16, the reagent(s) is deposited only on the portion of the electrode that is in the reaction zone to minimize the electrical resistance of the track 12c.

In the case of carbon being deposited to form the reference electrode 16 (i.e., an electrically conductive electrode without oxidation-reduction reagents), no additional material is required to be deposited on the surface of the reference electrode. The carbon can be doped with metal particles to increase the conductivity of the carbon.

Any electrically conductive material can be used to form the counter electrode 20. Preferred materials for forming the counter electrode 20 include, but are not limited to, platinum, palladium, carbon, gold, silver, and mixtures of silver and silver chloride (as in the reference electrode 16). In another embodiment, reagent(s) that forms the working ink can be deposited on the conductive material of the counter electrode 20. If the working ink is deposited on a conductive material to form the counter electrode 20, the reagent(s) is deposited only on the portion of the electrode that is in the reaction zone to minimize the electrical resistance of the track 12b.

Figure 7:
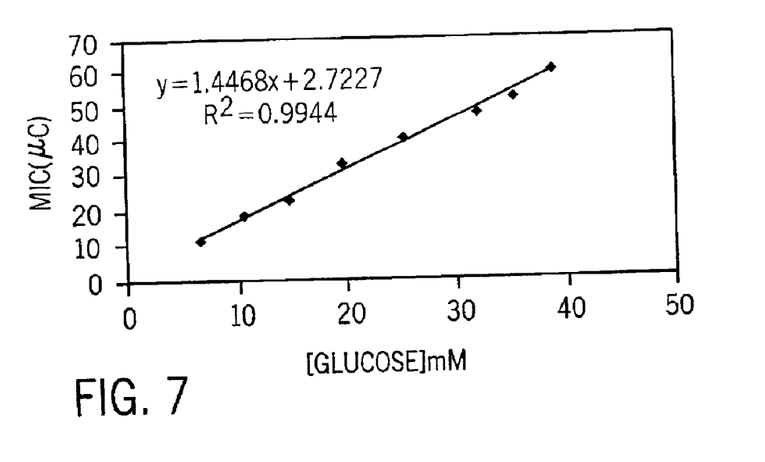
FIG. 7 is a graph depicting the relationship of the response of a biosensor strip of this invention as a function of the concentration of glucose, where the strip contains three electrodes, and the reference electrode comprises a layer of carbon and the counter electrode comprises a layer of carbon.

FIG. 7 shows the performance characteristics of a biosensor strip, where the strip contains three electrodes, and the reference electrode comprises a layer of carbon and the counter electrode comprises a layer of carbon.

The dimensions of the counter electrode 20 are preferably equal to or greater than those of the reference electrode 16. It is preferred that the counter electrode 20 be of a size equal to or greater than the working electrode 18, though this preference is not required at low levels of current. In functional terms, the size of the reference electrode is not critical; the size of the working electrode is selected on the basis of signal to noise ratio desired; the size of the counter electrode is selected to minimize resistance to current flow.

The counter electrode 20 must be in electrical contact with the working electrode 18 during the measurement. When current flows through the counter electrode 20, the flow of electrons produces an electrochemical reaction (a reduction reaction) sufficient to allow the electrons to flow. The counter electrode 20 must be positioned at a sufficient distance from the working electrode 18 so that the reactive species generated at the counter electrode 20 do not diffuse to the working electrode 18.

The reaction zone can have total area ranging from about 1 $mm^2$ to about 20 $mm^2$, preferably about 5 $mm^2$. The area of the working electrode typically ranges from about 0.5 to about 5 $mm^2$, preferably about 1.0 $mm^2$. The reference electrode and the counter electrode typically have areas ranging from about 0.2 to about 4.0 $mm^2$, preferably about 0.5 $mm^2$.

The biosensor strip 10 typically has a width of from about 4.5 to about 6.5 mm. The electrode support 11 can be made from any material that has an electrically insulating surface, such as, for example, polyvinyl chloride, polycarbonate, polyester, paper, cardboard, ceramic, ceramic-coated metal, and blends of these materials (e.g., a blend of polycarbonate and polyester).

Electrically conductive material can be applied to the electrode support 11 by a deposition method such as screen-printing. This deposit of electrically conductive material forms the contact areas 14a, 14b, and 14c, which areas allow the analyte monitor to interface with the biosensor strip 10. The conductive material further provides electrical connections between the contact areas and the active reagent(s) deposited on the electrode(s) of the biosensor strip 10. The formulation for the electrically conductive material can be an air-driable composition comprising carbon dispersed in an organic solvent. Alternative formulations include carbon dispersed in an aqueous solvent. Alternative electrically conductive materials that can be used in place of carbon include, but are not limited to, such materials as silver, gold, platinum, and palladium. Other methods of drying or curing the formulations containing the electrically conductive material include the use of infrared radiation, ultraviolet radiation, and radio frequency radiation. In an alternative method of application, the electrically conductive material can be deposited by means of a vapor deposition technique.

As stated previously, inks suitable for use in this invention can be screen-printed. Other ways of depositing the inks include drop coating, inkjet printing, volumetric dosing, gravure printing, flexographic printing, and letterpress printing. The electrically conductive portions of the electrodes are preferably screen-printed or deposited by means of sputtering or vapor deposition techniques. The reagents are preferably deposited by screen-printing or drop coating the formulations on the surface of the electrically conductive portion of the electrode. In the case of screen-printing, the reagents can be converted into particulate form wherein the particles contain carbon or silica, with carbon being preferred. In the drop coating formulation, the reagents can be mixed with a polymer (such as, for example, carboxy methyl cellulose, hydroxy ethyl cellulose, polyvinyl alcohol, etc.) solution to obtain a viscous solution, which is then dispensed on the area of interest. The inks can further include a polysaccharide (e.g., a guar gum, an alginate, locust bean gum, carrageenan, or xanthan), a hydrolyzed gelatin, an enzyme stabilizer (e.g., glutamate ortrehalose), a film-forming polymer (e.g., a polyvinyl alcohol, hydroxyethyl cellulose, polyvinyl pyrrole, cellulose acetate, carboxymethyl cellulose, and poly(vinyl oxazolidinone), a conductive filler (e.g., carbon), a defoaming agent, a buffer, or combinations of the foregoing. Other fillers for the inks include, but are not limited to, titanium dioxide, silica, and alumina.

It is preferred that the length of the path to be traversed by the sample (i.e., the reaction zone) be kept as short as possible in order to minimize the volume of sample required. With respect to the biosensor strip described herein, the volume of sample required is preferably no greater than 5 microliters, and more preferably ranges from about 0.5 microliters to about 2.5 microliters. The maximum length of the reaction zone can be as great as the length of the biosensor strip. However, the corresponding increase in resistance of the sample limits the length of the reaction zone to a distance that allows the necessary response current to be generated. Positioning the electrodes in the manner described herein has the further advantage of preventing completion of a circuit (and thus preventing detection of a response current) before the working electrode 18 has been completely covered by the sample.

Flow of the sample can be achieved by a chemical wicking method or by action of capillary forces. Chemical wicking can be achieved by using a fine grade surfactant coated mesh.

As shown in FIG. 1, a mesh layer 30 overlies the electrodes. As stated previously, this mesh layer 30 protects the printed components from physical damage, and the mesh layer 30 also helps the sample to wet the electrodes by reducing the surface tension of the sample, thereby allowing it to spread evenly over the electrodes. Preferably, this mesh layer 30 extends over the entire length of the reaction zone, between and including the position at which the sample is introduced and the region where the electrodes are disposed. Preferably, this mesh layer 30 is constructed of woven strands of polyester. Alternatively, any woven or non-woven material can be used, provided that it does not occlude the surface of the electrode such that normal diffusion of the sample is obstructed. The thickness of the mesh is selected so that the depth of the sample is sufficiently low that a high sample resistance is produced. Preferably, the mesh layer 30 is not more than 150 µm in thickness. Preferably the mesh layer 30 has a percent open area of about 35% to about 45%, a fiber count of about 40 per cm to about 60 per cm, a fiber diameter of about 70 µm to about 100 µm, and a thickness of from about 100 µm to about 160 µm. A particularly preferred mesh is PE130 HD mesh, available from Sefar (formerly ZBF), CH-8803, Ruschlikon, Switzerland.

The mesh layer 30 can be coated with a surfactant. A surfactant coating is necessary only if the material of the mesh layer 30 itself is hydrophobic (for example, nylon or polyester). If a hydrophilic mesh layer is used, the surfactant coating can be omitted. The particular choice of surfactant is not critical, so long as it allows sufficiently uniform spreading of the sample. A preferred surfactant is "FC 170C FLUORAD" fluorochemical surfactant (3M, St. Paul, Minn.). "FLUORAD" surfactant is a solution of a fluoro-aliphatic oxyethylene adduct, lower polyethylene glycols, 1,4-dioxane, and water. A surfactant loading of from about 15 to about 20 µg/mg of mesh is preferred for most applications. The preferred surfactant loading will vary depending on the type of mesh layer and surfactant used and the sample to be analyzed. The preferred surfactant loading can be determined empirically by observing flow of the sample through the mesh layer 30 with different levels of surfactant.

The mesh layer 30 can be held in place by the layer of hydrophobic electrically insulating material 24. This layer of electrically insulating material 24 is preferably applied by screen-printing the ink over a portion of the periphery of the mesh layer 30. Together, the mesh layer 30 and the layers of hydrophobic electrically insulating material 24 surround and define a reaction zone 30 suitable for the sample to travel from the position at which the sample is introduced at one end of the strip towards the reference electrode 16, then toward the working electrode 18, and then toward the counter electrode 20. The hydrophobic electrically insulating material 24 impregnates the mesh layer 30 outside of the reaction zone 30. The hydrophobic electrically insulating material 24 thus defines the reaction zone 30 by preventing the sample from infiltrating the portions of the mesh layer 30 covered by the layers of hydrophobic electrically insulating material 24. A hydrophobic electrically insulating material 24 preferred for impregnating the mesh layers is "SERICARD" (Sericol, Ltd., Broadstairs, Kent, UK). Another preferred hydrophobic electrically insulating material is commercially available as "POLYPLAST" (Sericol Ltd., Broadstairs, Kent, UK).

A layer of dielectric ink can optionally be applied to cover the majority of the printed carbon and silver/silver chloride tracks. In this case, two areas are left uncovered, namely the electrical contact areas and the sensing areas in the reaction zone. This layer of dielectric ink serves to define the area constituting the reaction zone, and to protect exposed tracks from short circuit.

As shown in FIG. 1, a cover 32 encloses the surfaces of the electrodes that are not in contact with the electrode support 11. The cover 32 is a liquid impermeable membrane. This cover 32 can be a flexible tape made of polyester or similar material. The cover 32 includes a small aperture 34 to allow access of the applied sample to the underlying mesh layer 30. This cover 32 encloses the exposed surfaces of the working electrode 18, the reference electrode 16, and the counter electrode 20. Thus, the cover 32 maintains the available sample space over the electrodes at a fixed depth, which is equivalent to the thickness of the mesh layer 30. The positioning of this cover 32 ensures that the resistance of the sample is maintained at a high level.

The aperture 34 is positioned to overlie an end of the mesh area upstream of the reference electrode 16, such that the exposed mesh area beneath the aperture 34 can be used as a point of access or application for a liquid sample, whereby the sample contacts the reference electrode 16 before the sample contacts the working electrode 18 and the counter electrode 20. Of course, the aperture 34 must overlie an end of the mesh area that is not covered by the hydrophobic electrically insulating ink 30. The size of this aperture 34 is not critical, but it should be sufficiently large to allow sufficient volume of sample to pass through to the mesh layer 30. The aperture 34 should not be so large as to allow any portion of the liquid sample to contact any of the electrodes before contacting the mesh layer 30. The aperture 34 can be formed in the liquid impermeable cover 32 by any suitable method (e.g., die punching).

The liquid impermeable cover membrane 32 can be affixed to the biosensor strip by means of a suitable method of adhesion. Preferably, affixing is achieved by coating the underside of the flexible tape with a layer of hot melt glue, and then heat welding the tape to the surface of the layer of hydrophobic electrically insulating ink 24. The layer of hot melt glue typically has a coating weight of from about 10 to about 50 $g/m^2$, preferably from about 20 to about 30 $g/m^2$. Pressure sensitive adhesives or other equivalent methods of adhesion may also be used. Care should be taken when the tape is applied, because the heat and pressure applied to the tape layer can melt the "SERICARD" ink and can cause it to smear onto adjoining areas. Care should also be taken so that the tape does not cover the electrodes, the reaction zone, or the area where the sample is applied.

The upper surface of the liquid impermeable cover 32 can also be provided with a layer of silicone or other hydrophobic material. This additional layer serves to drive the applied sample onto the portion of exposed mesh layer 30 at the sample application point, thereby rendering the application of small volumes of sample much simpler.

Figure 2:
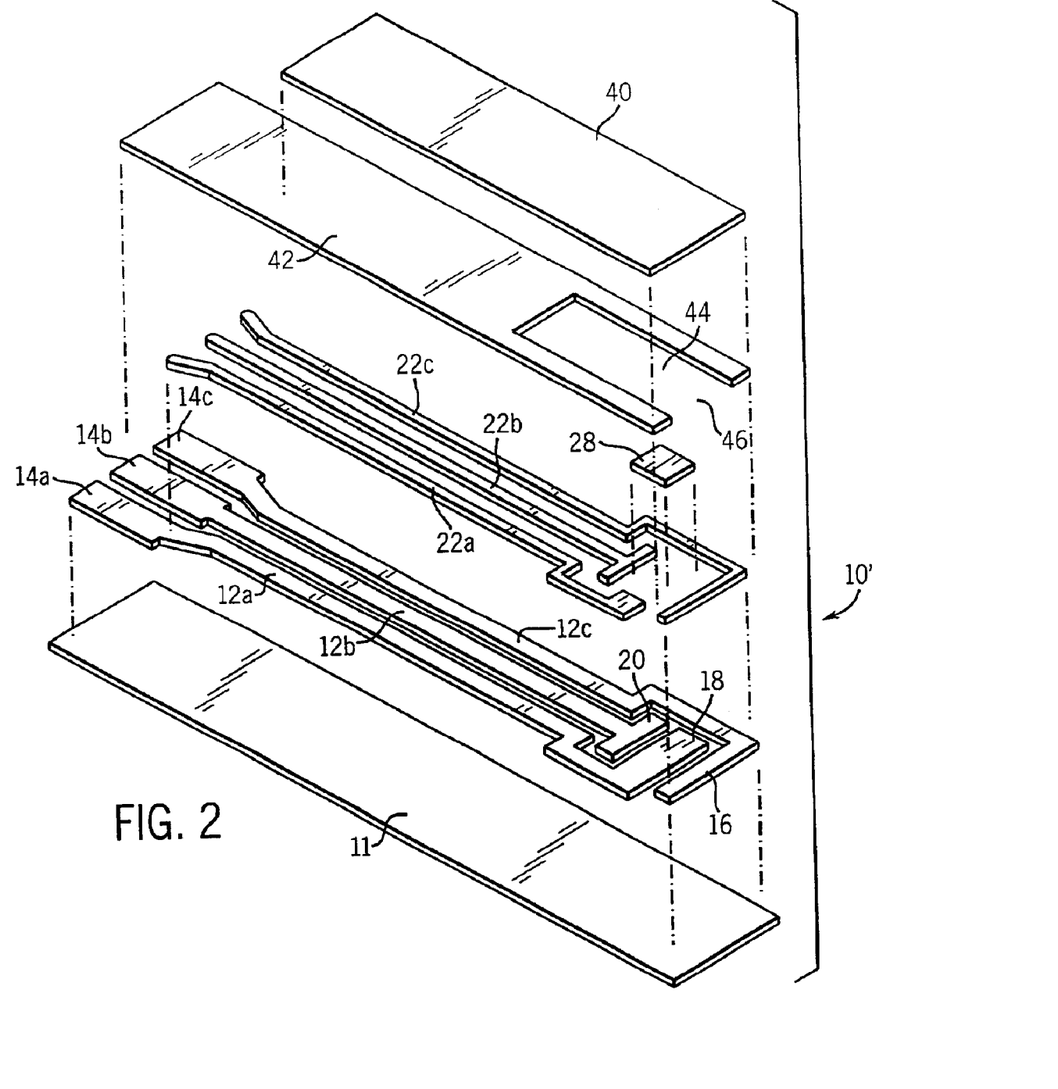
FIG. 2 is an exploded view of a biosensor strip according to another embodiment of this invention.
Figure 3A:
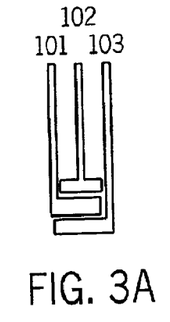
FIGS. 3A through 3E are schematic diagrams depicting the regions of a biosensor strip where the electrodes are disposed.
Figure 3B:
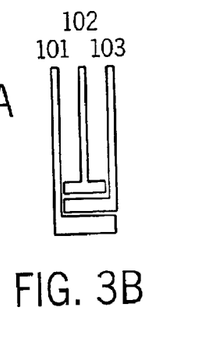
Figure 3C:
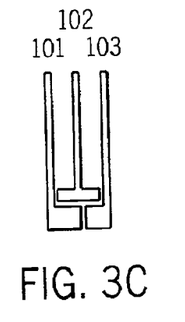
Figure 3D:
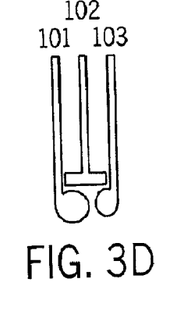
Figure 3E:
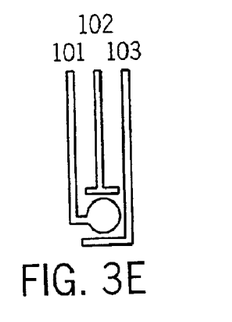

Flow by way of capillary force can be achieved by using a biosensor strip configuration of the type shown in FIG. 2. In the biosensor strip 10' shown in FIG. 2, the components represented by reference numerals 11, 12a, 12b, 12c, 14a, 14b, 14c, 16, 18, 20, 22a, 22b, 22c can be identical to those described previously, with respect to FIG. 1. The embodiment of the biosensor strip 10' shown in FIG. 2 employs a cover layer 40 and a spacer layer 42, such as, for example, a layer of adhesive, between the electrode support 11 and the cover layer 40 of the biosensor strip 10'. The adhesive can be a pressure sensitive adhesive. Pressure sensitive adhesives suitable for forming the spacer layer are commercially available and well-known to one of ordinary skill in the art. The cover layer 40 does not have an aperture. The spacer layer 42 has a slot 44 that provides the boundary of the reaction zone, in a manner somewhat analogous to the function of the opening 26 in providing the boundary for the reaction of the biosensor strip 10. The biosensor strip 10' does not have a mesh layer. The liquid sample enters the biosensor strip 10' via an opening 46 formed at one end of the slot 44 at one end of the biosensor strip 10'. The liquid sample is introduced at the opening 46 and reaches and traverses the reaction zone by means of the action of capillary force. In the embodiments that employ a cover layer 40, the cover layer 40 can be made from the same type of material that is suitable for making the electrode support 11.

Figure 9:
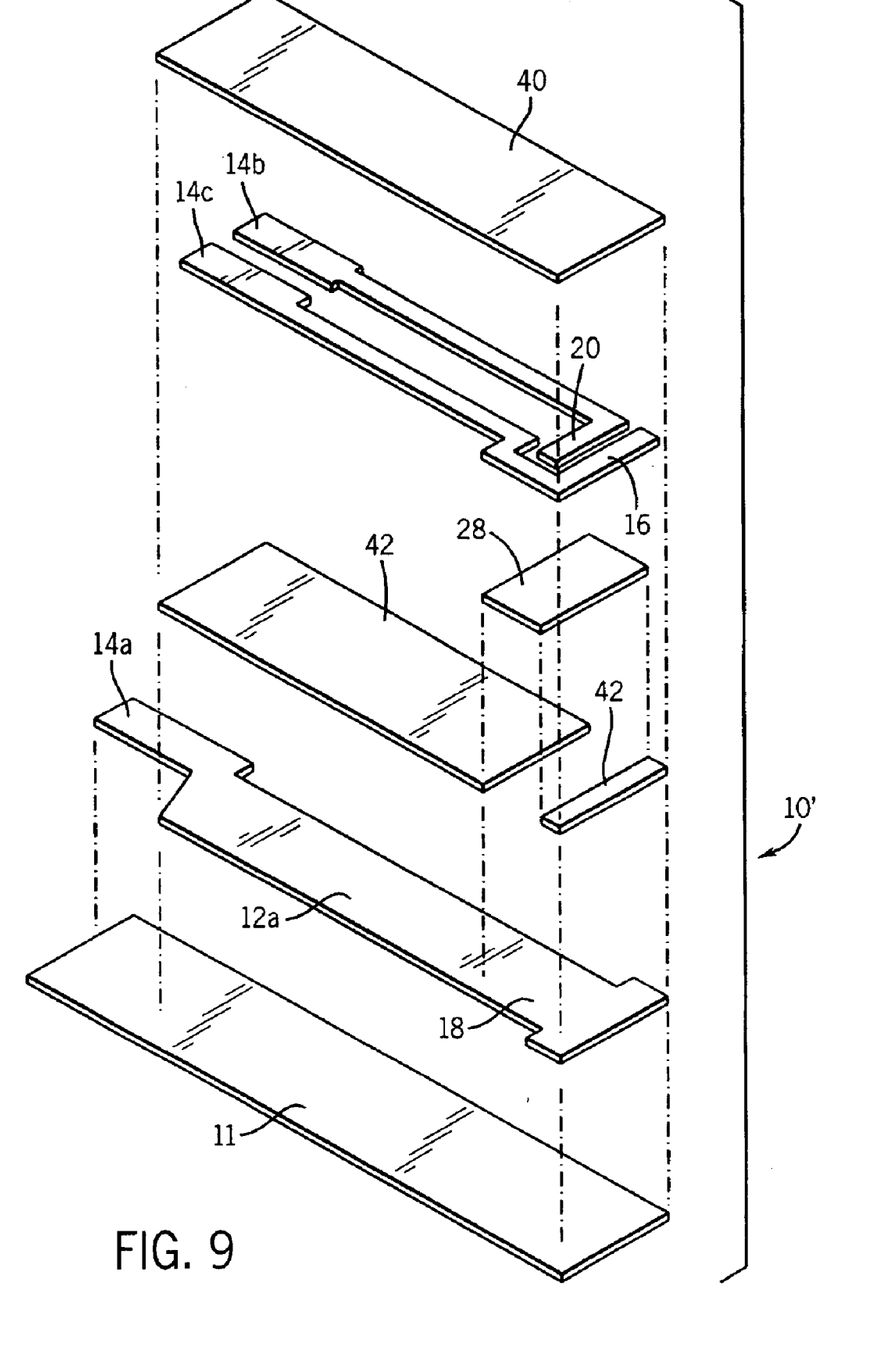
FIG. 9 is an exploded view of a biosensor strip according to another embodiment of the invention.

In the embodiment of the biosensor strip 10' shown in FIG. 9, the electrodes 16, 18, and 20 need not all be applied to the electrode support 11. At least one of the electrodes should be applied to the electrode support 11. However, at least one of the two remaining electrodes can be applied to the cover layer 40, in which case, the electrode or electrodes applied to the cover layer 42 would be between the cover layer 40 and the spacer layer 42. The only requirement is that the sample should be able to contact all three electrodes in the reaction zone.

FIGS. 3A through 3E illustrate six different configurations of the electrode regions of the biosensor strips of this invention. In FIGS. 3A through 3E, the working electrode is represented by the reference numeral 101, the counter electrode is represented by the reference numeral 102, and the reference electrode is represented by the reference numeral 103.

In use, a biosensor strip 10 of this invention is connected, via electrode contacts 14a, 14b, and 14c, to a measuring device (not shown). A liquid sample is applied through aperture 34, and the sample moves along the reaction zone. The progress of the sample is sufficiently impeded by the mesh layer 30, thereby allowing the sample to form a uniform flow front. Air is displaced through the upper portion of the mesh layer 30 to and through the aperture 34. The sample first completely covers the working electrode 18 and the reference electrode 16, and only then approaches and covers and the counter electrode 20, thereby completing the circuit and causing a response to be detected by the measuring device. The biosensor strip 10' is used in the same manner as is the biosensor strip 10, except that the sample is applied at the opening 46 and reaches and traverses the reaction zone by means of the action of capillary force. Measuring devices that are suitable for use in this invention include any commercially available analyte monitor that can accommodate a biosensor strip having a working electrode, a reference electrode, and a counter electrode. Such analyte monitors can be used to monitor analytes, such as, for example, glucose and ketone bodies. In general, such a monitor must have a power source in electrical connection with the working electrode, the reference electrode, and the counter electrode. The monitor must be capable of supplying an electrical potential difference between the working electrode and the reference electrode of a magnitude sufficient to cause the electrochemical oxidation of the reduced mediator. The monitor must be capable of supplying an electrical potential difference between the reference electrode and the counter electrode of a magnitude sufficient to facilitate the flow of electrons from the working electrode to the counter electrode. In addition, the monitor must be capable of measuring the current produced by the oxidation of the reduced mediator at the working electrode.

In the method of this invention, the liquid sample can be a sample of whole blood. In other test strips suggesting the use of three electrodes, the liquid sample is whole blood that has been filtered or treated to remove red blood cells or other hemocytes.

In a measurement employing a biosensor strip 10, a constant voltage is applied at the working electrode and the current is measured as a function of time. This technique is known as chronoamperometry. The voltage applied should be equal or higher to the voltage required to oxidize the reduced mediator. Thus, the minimum voltage required therefore is a function of the mediator.

The sample is responsible for the solution resistance. The solution resistance inhibits the flow of electrons. The effect of solution resistance on the measurement is minimized by this invention. Arranging the electrodes close together obviously minimizes the effect of solution resistance because solution resistance is a function of the spacing between the electrodes. By allowing the current to flow through a different electrode, the effect of solution resistance on the working electrode can be minimized.

In an amperometric measurement, the current should decay with time according to the Cottrell equation.

$$i_t = \frac{nFAC_oD_o^{1/2}}{\pi^{1/2}t^{1/2}}$$

where
$i_t$=the current at time t
n=number of electrons
F=Faraday's constant
A=area of the electrode
$C_O$=bulk concentration of the electrochemically active species
$D_O$=diffusion coefficient of the electrochemically active species Therefore, $i_t t^{1/2}$ should be a constant.

In an amperometric measurement, a constant voltage is applied at the working electrode with respect to the reference electrode, and the current between the working and counter electrodes is measured. The response of the biosensor strip has two components, catalytic (glucose response component) and Faradaic (solution resistance component). If the resistance of the solution is minimized, the response of the biosensor strip at any given time will have substantially higher glucose response component, as compared with the solution resistance component. Therefore, one is able to obtain good correlation with the concentration of glucose from the response of the biosensor strip even at assay times as short as one second. If the resistance of the solution is high, the voltage experienced at the working electrode will lag significantly from the voltage applied. This lag is significantly higher for a two-electrode system, as compared with a three-electrode system. In the case of two-electrode system, the value of iR between the working and the reference electrode is significantly higher than that in a three-electrode system. In a three-electrode system, no current flows between the working electrode and the reference electrode, and hence the voltage drop is lower. Therefore, once the charging current (Faradaic current) decays to a minimum (within two to three milliseconds), the current observed is all catalytic current. In a two-electrode system, the charging current is not diminished until the voltage at the working electrode attains a steady state (reaches the applied voltage). Thus, in a two-electrode system, there is a slow decay of the response profile.

The shortest assay time currently available is five seconds. This assay time is available with a two-electrode system. Other systems with assay times as short as 10 seconds are available. In the three-electrode system described herein, substantially instantaneous assay times are feasible.

A shorter assay time, combined with a reduced sample volume, is preferred by the consumer. Instantaneous assay times can lead to such developments as biosensor on a needle, which does not require the drawing of blood.

The biosensor strip of this invention has cost advantages. The concentrations of the enzyme and the mediator are low, thereby minimizing the cost of these materials. In addition, the biosensor strip does not require a mixture of silver and silver chloride to be printed on the reference electrode, if the working ink is applied to the reference electrode. The elimination of this requirement reduces material costs, as well as subtracting one step from the manufacturing process.

Figure 4:
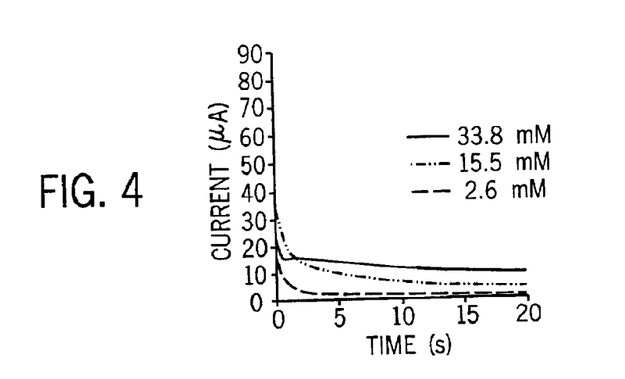
FIG. 4 is a graph depicting response curves of a biosensor strip having two electrodes—a working electrode and a dual-purpose reference/counter electrode.
Figure 5:
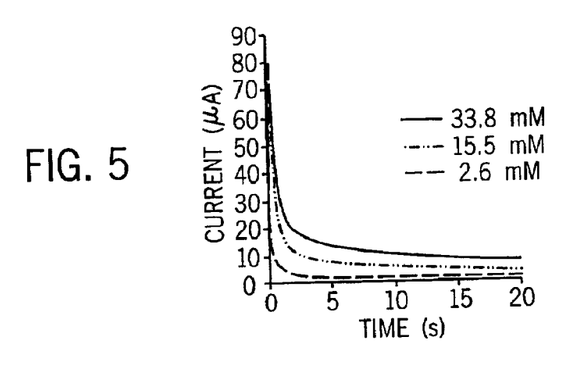
FIG. 5 is a graph depicting response curves of a biosensor strip having three electrodes—a working electrode, a reference electrode, and a counter electrode.
Figure 6:
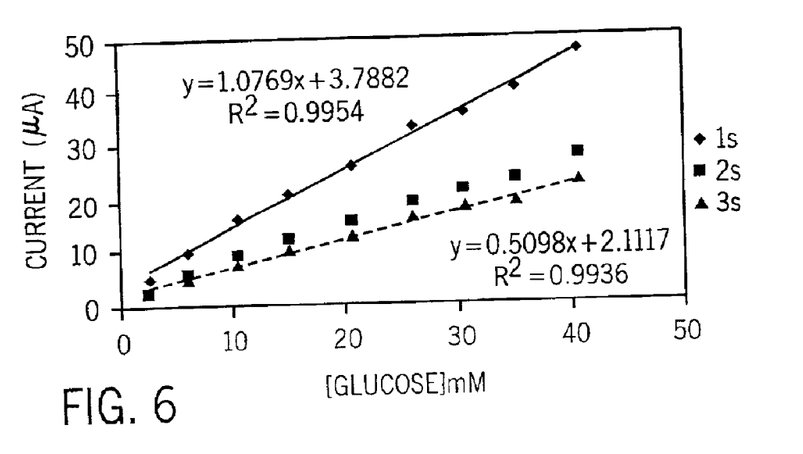
FIG. 6 is a graph depicting the relationship of the response of a biosensor strip of this invention as a function of the concentration of glucose at different points in time in an assay.

In order to show the advantages of the biosensor strip of this invention, voltage of 200 mV was applied at the working electrode with respect to the reference electrode, and the response between the working electrode and the counter electrode was measured. FIG. 4 shows the response for a biosensor strip having two electrodes as a function of time for three different concentrations of glucose. FIG. 5 shows the response for a biosensor strip having three electrodes as a function of time for three different concentrations of glucose. The measurement response curves of a biosensor strip having two electrodes do not spike as high as do those of a biosensor strip having three electrodes. FIG. 6 shows the responses as a function of concentration of glucose at the end of 1 second, 2 seconds, and 3 seconds for a biosensor strip having three electrodes. The correlation of response of the biosensor strip with the concentration of glucose is very good, thereby indicating that one can accurately measure the concentration of glucose in samples at times as short as one second after the start of the assay. This benefit results from the rapid decay of the response curve.

Electroactive species are chemical compounds that undergo electrochemical oxidation at the working electrode. These compounds are also referred to as interfering agents. The oxidation of these compounds at the electrode surface adds to the current generated by the glucose oxidation and hence results in an elevated glucose response. Examples are uric acid, ascorbic acid, acetaminophen, gentisic acid, and the like. As the voltage at the working electrode is increased, more and more of these compounds become oxidized. The additional signal resulting from the oxidation of these interfering agents results in an elevated glucose response. Thus, the applied voltage in a measurement is a compromise between the desired potential for efficient oxidation of the compound of interest and the minimization of the interference from compounds in the sample that are not of interest. Therefore, the lower voltage requirement of this invention results in the reduction of interference.

The electrochemical oxidation of a compound (e.g., a reduced mediator) occurs at a voltage referred to as oxidation potential. However, in all chronoamperometry experiments, a potential higher than the oxidation potential is applied. This difference between the oxidation potential and the actual potential required to carry out the reaction is designated over-potential. The over-potential represents the extra energy needed to force a slow reaction to proceed at a desired rate.

As explained earlier, in a two-electrode system, the voltage experienced at the working electrode is lower than that applied. This situation calls for the application of higher voltage than that required for efficient oxidation of the reduced mediator under conditions such as higher hematocrit levels. Application of higher voltage is not required in a three-electrode system.

A biosensor strip having three electrodes does not require a good reference electrode because no current flows in the reference circuit; hence, there is no drift in the applied potential at the working electrode.

This invention also demonstrates that an electrically conductive electrode in contact with a reagent system containing enzyme and mediator can also be used as a reference electrode. In the prior art that involves a substantially end point measurement, the concentration of the oxidized form of the mediator is maintained at very high level so that the enzymatic reduction of the mediator (resulting from oxidation of glucose) does not change the ratio of the reduced form of the mediator to the oxidized form of the mediator significantly. In this invention, the concentration of the mediator can be maintained at a low concentration, because of limited solubility, and the reference electrode thus formed does serve as a satisfactory reference electrode.

EXAMPLES

The following examples are intended to be illustrative and not limiting of the invention.

Example 1

This example illustrates the chemical composition of a working ink for the measurement of the concentration of glucose.

In this example, the formulation of the working ink for the working electrode comprises, as active components, glucose dehydrogenase as the enzyme, a nicotinamide adenine dinucleotide as a coenzyme, and a phenanthroline quinone as the mediator. The inactive components include buffer (to maintain the pH during ink preparation), a binder (hydroxyethyl cellulose), a protein stabilizer (trehalose), a stabilizer for glucose dehydrogenase (bovine serum albumin), an antifoaming agent (clerol), a salt (magnesium chloride), and carbon (conducting particulate additive). Magnesium chloride aids the solubility of the mediator during reaction. Ranges of these ingredients that are suitable for this invention are shown in Table 1.

TABLE 1

| Ingredient | Amount |
| --- | --- |
| Enzyme (such as glucose dehydrogenase or 3-hydroxybutyrate dehydrogenase) | 200 to 4000 Units |
| Nicotinamide coenzyme (such as $NAD^+$) | 5 to 30 weight percent |
| Mediator (such as 1,10-phenanthroline quinone) | 0.1 to 1.5 weight percent |
| Buffer | 50 to 100 mM |
| Antifoaming agent | 2 to 4 weight percent |
| Salt | 10 to 300 mM |
| Filler (such as ultra fine carbon or titania) | 10 to 30 weight percent |
| Binder (such as alginate or guar gum, hydroxyethyl cellulose) | 0.01 to 0.5 weight percent |
| Protein stabilizer (such as trehalose or bovine serum albumin) | 0.01 to 2 weight percent |

Example 2

This example illustrates the chemical composition of a working ink for the measurement of the concentration of ketone bodies.

In this example, the formulation of the working ink for the working electrode comprises, as the active components, a 3-hydroxybutyrate dehydrogenase as the enzyme, a nicotinamide adenine dinucleotide as a coenzyme, and a phenanthroline quinone as the mediator. The inactive components include buffer (to maintain the pH during ink preparation), binder (guar gum), antifoaming agent (clerol), salt (magnesium chloride), carbon (conducting particulate additive), and a protein stabilizer. Ranges of concentrations of these ingredients per gram of the working ink that are suitable for this invention are also shown in Table 1.

Example 3

This example illustrates another embodiment of the chemical composition of a working ink for the measurement of the concentration of glucose.

In this example, the formulation of the working ink for the working electrode comprises, as the active components, glucose oxidase as the enzyme and a ferrocene derivative as the mediator. The inactive components are buffer (to maintain the pH during the ink preparation), binders (polyvinyl alcohol, alginate), antifoaming agent (clerol), carbon (conducting particulate additive), and a protein stabilizer. Ranges of concentrations of these ingredients per gram of the working ink that are suitable for this invention are shown in Table 2.

TABLE 2

| Ingredient | Amount |
| --- | --- |
| Enzyme (such as glucose oxidase) | 200–4000 units |
| Mediator (such as ferrocene; 4,7-phenanthroline quinone) | 0.1 to 1.5 weight percent |
| Buffer | 50 to 100 mM |
| Antifoaming agent | 2 to 4 weight percent |

TABLE 2-continued

| Ingredient | Amount |
| --- | --- |
| Filler (such as ultra fine carbon or titania) | 10 to 30 weight percent |
| Binder (such as alginate or guar gum, hydroxyethyl cellulose) | 0.01 to 0.5 weight percent |
| Protein stabilizer (such as trehalose) | 0.01 to 2 weight percent |

Example 4

This example illustrates another embodiment of the chemical composition of working ink for the measurement of the concentration of glucose.

In this example, the formulation of the working ink for the working electrode comprises, as the active components, glucose oxidase as the enzyme and a potassium ferricyanide as the mediator. The inactive components are buffer (to maintain the pH during the ink preparation), a binder such as a cellulosic material, a filler such as silica, an antifoaming agent (clerol), and a protein stabilizer. Ranges of concentrations of these ingredients per gram of the working ink that are suitable for this invention are shown in Table 3.

TABLE 3

| Ingredient | Amount |
| --- | --- |
| Enzyme (such as glucose oxidase) | 200–4000 units |
| Mediator (such as potassium ferricyanide) | 0.1 to 1.5 weight percent |
| Buffer | 50 to 100 mM |
| Antifoaming agent | 2 to 4 weight percent |
| Filler (such as silica or titania) | 10 to 30 weight percent |
| Binder (such as alginate or guar gum, hydroxyethyl cellulose) | 0.01 to 0.5 weight percent |
| Protein stabilizer (such as trehalose) | 0.01 to 2 weight percent |

Example 5

This example describes a method for fabricating a biosensor strip that employs the working ink described in Examples 1, 2, and 3.

Three tracks of conductive material 12a, 12b, and 12c are printed on one surface of an electrode support 11. The ink for preparing the conductive tracks comprises a conductive material, such as conductive carbon, platinum, palladium, gold, or semiconductive material such as indium doped tin oxide. A mixture of silver and silver chloride is printed on each conductive track, but neither the contact areas 14a, 14b, and 14c nor the area of the working electrode 18 in the reaction zone are printed with the silver/silver chloride mixture. The layer of working ink 28 is printed on the area of the working electrode 18 that is in the reaction zone. A layer of hydrophilic mesh 30 is placed over the reaction zone. An insulating layer 24 is used to cover the entire biosensor strip, except for the contact areas 14a, 14b, and 14c and the reaction zone. A tape 32 having an aperture 34 is positioned over the mesh layer 30 to define the volume of sample to be used.

Example 6

This example describes a method for fabricating a biosensor strip that employs the working ink described in Examples 1, 2, and 4.

Three tracks of conductive material 12a, 12b, and 12c are printed on one surface of an electrode support 11. The ink for preparing the conductive tracks comprises a conductive material, such as conductive carbon, platinum, palladium, gold, or semiconductive material such as indium doped tin oxide. The layer of working ink 28 is printed on the area of the working electrode 18 in the reaction zone and on the area of the reference electrode 16 in the reaction zone. A layer 30 of hydrophilic mesh is placed over the reaction zone. An insulating layer 24 is used to cover the entire test strip, except for the contact areas 14a, 14b, and 14c and the reaction zone. A tape 32 having an aperture 34 is positioned over the mesh layer 30 to define the volume of sample to be used.

Figure 8:
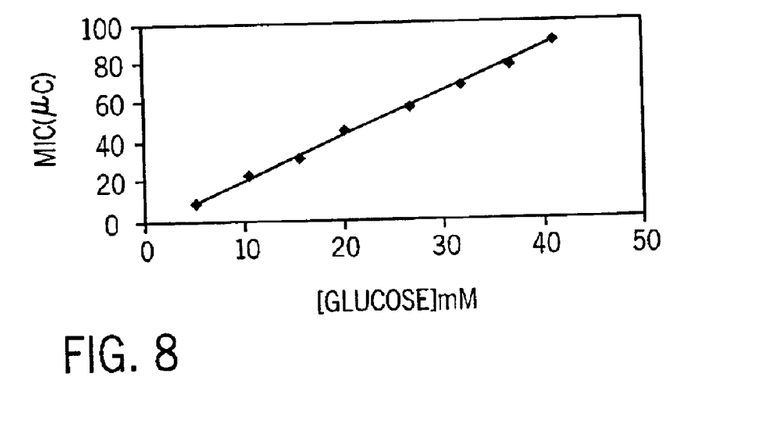
FIG. 8 is a graph depicting the relationship of the response of a biosensor strip of this invention as a function of the concentration of glucose, where the strip contains three electrodes, and the reference electrode comprises a layer of carbon on which is printed layer comprising glucose dehydrogenase, nicotinamide cofactor, and 1,10-phenanthroline quinone.

A biosensor strip prepared according to this example has performance characteristics similar to those shown in FIG. 8.

Example 7

This example describes a method for fabricating a biosensor strip that employs the working ink described in Example 4.

Three tracks of conductive material 12a, 12b, and 12c are printed on one surface of an electrode support 11. The ink for preparing the conductive tracks comprises a conductive material, such as conductive carbon, platinum, palladium, gold, or semiconductive material such as indium doped tin oxide. The layer of working ink 28 is printed in the reaction zone (i.e., the working ink can cover all three electrodes). A layer 30 of hydrophilic mesh is placed over the reaction zone. An insulating layer 24 is used to cover the entire test strip, except for the contact areas 14a, 14b, and 14c and the reaction zone. A tape 32 having an aperture 34 is positioned over the mesh layer 30 to define the volume of sample to be used.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A biosensor strip for determining the concentration of an analyte in a sample of biological liquid, said biosensor strip comprising:
   (a) an electrode support having an electrode bearing major surface;
   (b) a cover layer having an electrode-bearing major surface;
   (c) a spacer layer interposed between said electrode support and said cover layer;
   (d) a first electrode, said first electrode being a working electrode, said working electrode comprising working ink comprising (i) a reagent responsive to said analyte in said sample of said biological liquid and (ii) an electron mediator deposited on an electrically conductive material;
   (e) a second electrode, said second electrode being a reference electrode, said reference electrode comprising (i) said reagent responsive to said analyte in said sample of said biological liquid and (ii) said electron mediator deposited on an electrically conductive material; and
   (f) a third electrode, said third electrode being a counter electrode, said counter electrode comprising an electrically conductive material, said electrode-bearing major surface of said first electrode support facing said electrode-bearing major surface of said cover layer.

2. The biosensor strip of claim 1, wherein said reference electrode comprises a conductive material.

3. The biosensor strip of claim 1, wherein said reagent responsive to said analyte in said sample of said biological liquid is an enzyme.

4. The biosensor strip of claim 3, wherein said enzyme is selected from the group consisting of glucose oxidase and glucose dehydrogenase.

5. The biosensor strip of claim 1, wherein said electron mediator is a ferricyanide salt.

6. The biosensor strip of claim 1, wherein said electron mediator is ferrocene or a derivative thereof.

7. The biosensor strip of claim 1, wherein said electron mediator is a phenanthroline quinone or a derivative thereof.

8. The biosensor strip of claim 1, wherein said spacer layer comprises an adhesive.

9. The biosensor strip of claim 8, wherein said adhesive is a pressure sensitive adhesive.

10. The biosensor strip of claim wherein at least one of said three electrodes is disposed on said electrode support and at least one of said remaining two electrodes is disposed on said cover layer.

11. The biosensor strip of claim 1, wherein said counter electrode is positioned relative to said working electrode and said reference electrode such that a liquid sample will contact said working electrode and said reference electrode prior to contacting said counter electrode.

12. A method for determining the concentration of an analyte in a sample of biological liquid, said method comprising the steps of:

(a) providing the biosensor strip of claim 1;

(b) applying said biological liquid to said biosensor strip;

(c) inserting said biosensor strip into an analyte monitor;

(d) applying a voltage at the working electrode with respect to the reference electrode;

(e) measuring the current flowing between the working electrode and the counter electrode; and (f) correlating the current measured to the concentration of said analyte.

* * * * *

UNITED STATES PATENT AND TRADEMARK OFFICE
CERTIFICATE OF CORRECTION

PATENT NO. : 6,863,800 B2  Page 1 of 1
DATED : March 8, 2005
INVENTOR(S) : Shridhara Alva Karinka et al.

It is certified that error appears in the above-identified patent and that said Letters Patent is hereby corrected as shown below:

Column 17,
Line 17, replace "claim" with -- claim 1 --.

Signed and Sealed this

Seventh Day of February, 2006

JON W. DUDAS
*Director of the United States Patent and Trademark Office*